US00PP27596P3

(12) United States Plant Patent
Travers

(10) Patent No.: US PP27,596 P3
(45) Date of Patent: Jan. 24, 2017

(54) ***CLEMATIS* PLANT NAMED 'TRA35'**

(50) Latin Name: ***Clematis* hybrid**
Varietal Denomination: TRA35

(71) Applicant: Bernard Travers, Saint Cyr en Val (FR)

(72) Inventor: Bernard Travers, Saint Cyr en Val (FR)

( * ) Notice: Subject to any disclaimer, the term of this patent is extended or adjusted under 35 U.S.C. 154(b) by 89 days.

(21) Appl. No.: 14/544,082

(22) Filed: Nov. 24, 2014

(65) Prior Publication Data

US 2016/0150709 P1 May 26, 2016

(51) Int. Cl.
*A01H 5/02* (2006.01)

(52) U.S. Cl.
USPC ..... Plt./228

(58) Field of Classification Search
USPC ..... Plt./228
See application file for complete search history.

(56) References Cited

PUBLICATIONS

UPOV—International Union for the Protection of New Varieties of Plants, PLUTO:Plant Variety Database; Apr. 14, 2016; citation for 'TRA35' (1 pg. total).*

* cited by examiner

*Primary Examiner* — Susan McCormick Ewoldt
(74) *Attorney, Agent, or Firm* — Cassandra Bright

(57) ABSTRACT

A new and distinct *Clematis* hybrid named 'TRA35' is disclosed, characterized by a very large flowers, up to 22 to 30 cm in diameter. Flowers have uniquely elontaged tepal shapes, and a violet-blue coloration, with a pink median streak. The new cultivar is a *Clematis* typically suited for ornamental container and landscape use.

2 Drawing Sheets

Figure 1:
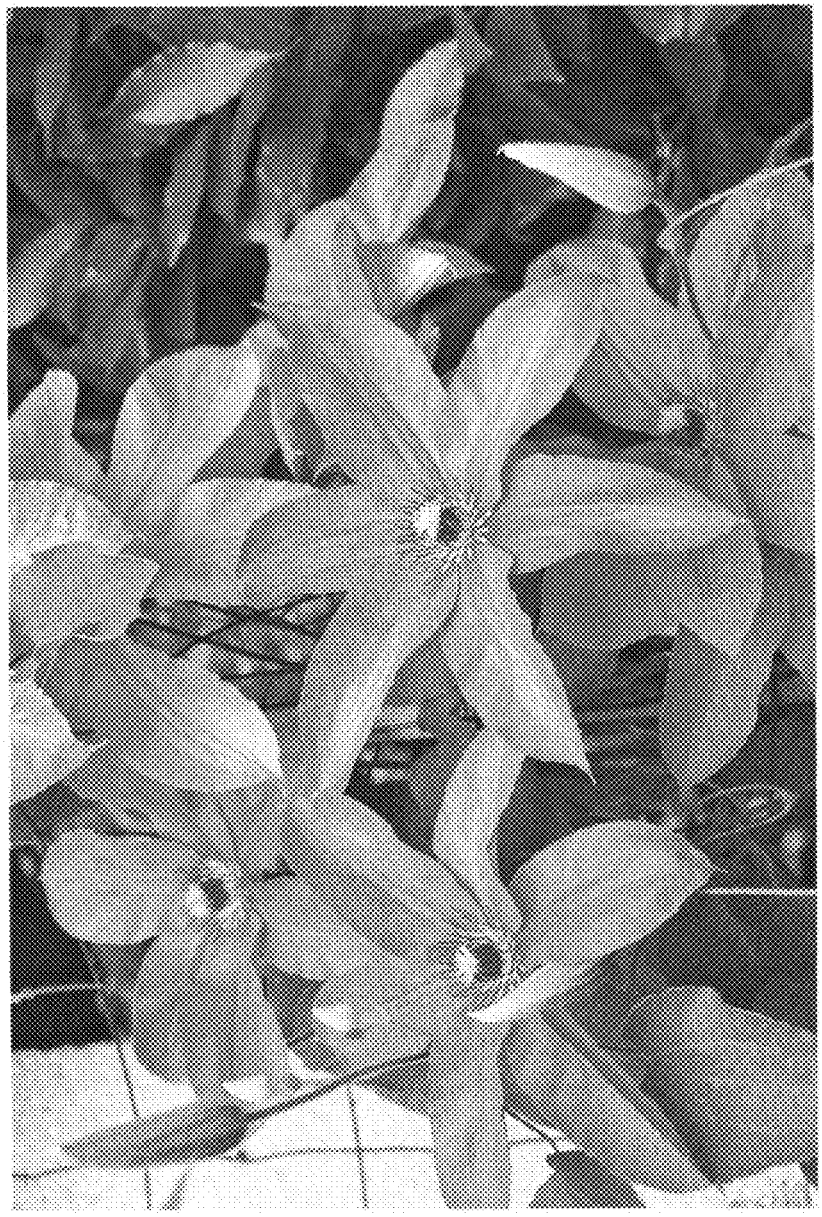

Latin name of the genus and species: *Clematis* hybrid.
Variety denomination: 'TRA35'.

BACKGROUND OF THE INVENTION

The new cultivar is the result of a breeding program, with the objective to develop new varieties of *Clematis* with strong growth and interesting flowers for commercial purposes. The new variety was discovered as a single plant among a group of seedlings of unknown parentage observed by the inventor, Bernard Travers. The discovery was made during 2004. Discovery was made at a commercial nursery in Orleans, France.

After selecting and isolating the new cultivar, asexual reproduction of the new cultivar 'TRA35' was first performed at a commercial nursery in St. Jean Le Blanc by vegetative cuttings during 2005. The inventor maintained the original plant, and observed the clones for several years, to establish stability of the characteristics. 'TRA35' has since produced multiple generations and has shown that the unique features of this cultivar are stable and reproduced true to type. Public access to plant material first occurred during early Spring of 2014. Before this time, plant material was under the control of the inventor, or those directly authorized by the inventor. This variety is described in CPVO application no A201302537. A copy of this application and technical question are included with the mailing of this application. Page 5 of the application verifies at the time of the EU application sales had not occurred either in the EU or any other country. Neither the EU application, nor any other publication resulted in an enabling disclosure of 'TRA35'.

SUMMARY OF THE INVENTION

The cultivar 'TRA35' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'TRA35.' These characteristics in combination distinguish 'TRA35' as a new and distinct *Clematis* cultivar:

1. Very large flowers with a diameter of 22 to 30 cm
2. Elongated tepal shape.
3. Violet-blue flowers with pink center streaks

PARENTAL COMPARISON

Parent varieties are unknown, the breeder is unable to supply records of the crossings.

COMMERCIAL COMPARISON

Plants of the new cultivar 'TRA35' can be compared to the known commercial variety *Clematis* hybrid 'Sympathia' unpatented. The *Clematis* varieties are similar in most horticultural characteristics, however 'TRA35' differs from 'Sympathia' in the following:

1. 'TRA35' has violet-blue flowers, with a pink center streak, whereas this comparator has two-tone pink flowers.
2. 'TRA35' has elongated tepals, this comparator has broad, obovate shaped tepals.

Plants of the new cultivar 'TRA35' can be compared to the known commercial variety *Clematis* 'Doctor Ruppel', unpatented. The *Clematis* varieties are similar in most horticultural characteristics. 'TRA35' differs from the comparator in the following:

1. 'TRA35' has violet-blue flowers, with a pink center streak, whereas this comparator has two-tone pink flowers.
2. 'TRA35' produces a larger flower of 22 to 30 cm, compared to a typically flower of 'Doctor Ruppel', which is 18 to 22 cm.

BRIEF DESCRIPTION OF THE PHOTOGRAPHS

The accompanying photograph in FIG. 1 illustrates in full color a typical flowers and foliage of 'TRA35'.

Figure 2:
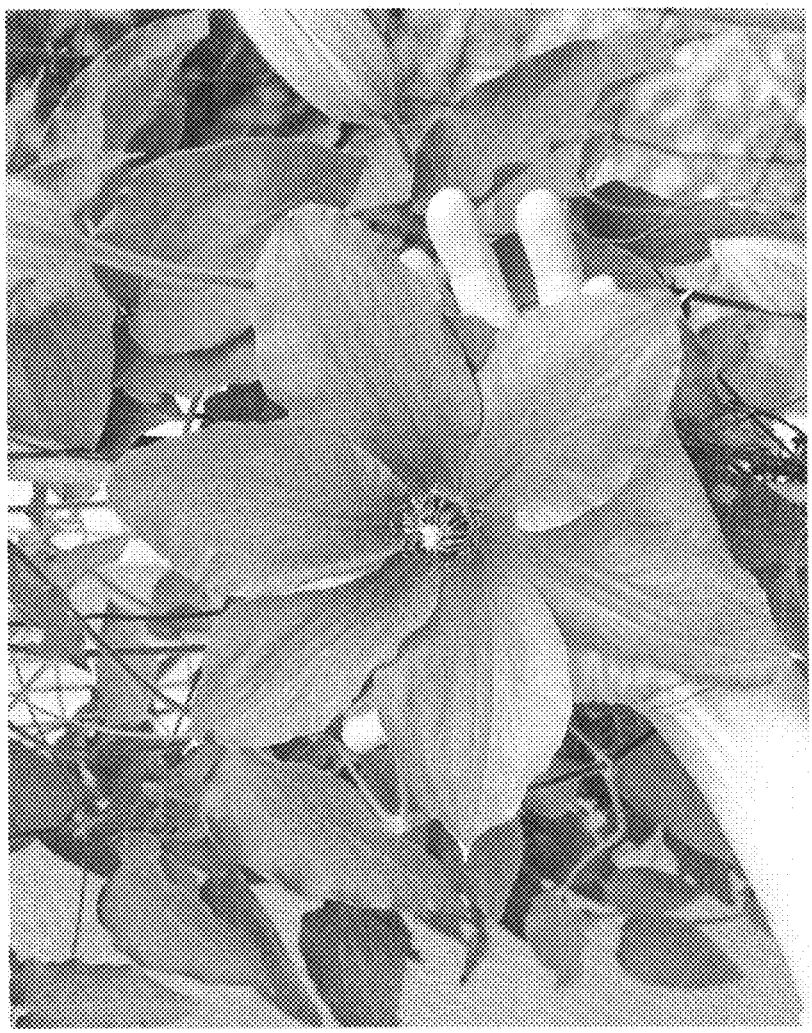

FIG. 2 depicts an individual flower of 'TRA35'.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007, except where general terms of ordinary dictionary significance are used. The following observations and measurements describe 'TRA35' plants grown outdoors in Saint Cyr en Val, France. The growing temperature ranged from approximately −2° C. to 25° C. at night to 8° C. to 33° C. during the day. No artificial light, photoperiodic treatments or chemical treatments were given to the plants. Measurements and numerical values represent averages of typical flowering types.

Botanical classification: *Clematis* hybrid 'TRA35'.

Age of the plant described: Approximately 8 months.

PROPAGATION

Typical method: Vegetative cuttings.

Time to initiate rooting: Approximately 20 days at 21° C. or higher.

Time to produce a rooted plantlet: Approximately 40 days at 20° C. or higher.

Root description: Fine, fibrous.

PLANT

Growth habit: Climbing vine.

Height: Approximately 200 cm.

Plant spread: Approximately 100 cm.

Growth rate: Moderate to rapid. During active growing season in Spring, approximately 80 cm per month.

Branching characteristics: One main stem.

Length of main stem: Approximately 200 cm.

Diameter of main stem: Approximately 0.2 to 0.5 cm.

Main stem color: Near RHS Greyed-Purple 187A.

Main stem texture: Glabrous.

Internode length: Approximate range 7 cm to 15 cm.

Strength: Strong, flexible, semi-woody.

FOLIAGE

*Arrangement*.—Opposite, mostly compound trifoliate occasionally single.

*Overall leaf length*.—Approximately 22 cm long.

*Overall leaf diameter*.—Approximately 14 cm.

*Leaflets*.—Average Length: approximately 8.6 cm. Average Width: approximately 4.4 cm. Shape of blade: Lanceolate. Apex: Acute. Base: Cordate to obtuse.

*Attachment*.—Stalked, twining leaf petiole.

*Margin*.—Entire.

*Texture of upper surface*.—Smooth with distinctly hirsute veins.

*Texture of lower surface*.—Rugose, slightly pubescent toward margin.

*Color*.—Young foliage upper side: Near RHS Green 137C. Young foliage under side: Near RHS Yellow-Green 144A. Mature foliage upper side: Near RHS Green 137B. Mature foliage under side: Near RHS Green 143B.

*Venation*.—Type: Pinnate. Venation color upper side: Near RHS Yellow-Green 144A. Venation color under side: Near RHS Yellow-Green 144A.

Petiole:

*Length*.—Range from 2.0 to 6.5 cm.

*Diameter*.—Approximately 0.1 to 0.3 cm.

*Texture*.—Hirsute.

*Color*.—Near RHS Green 138C, with Greyed-Purple N187A.

FLOWER

Bloom period:

*Natural season*.—First flush of flowers occur May through June, then a second flush occurs September.

Inflorescence type and habit: Axillary occurring; 1 flowers facing outward.

Rate of flower opening: Approximately 7 days from bud to fully opened flower.

Flower longevity on plant: Approximately 8 to 12 days, after fully opened. Self-cleaning.

Inflorescence size:

*Diameter*.—Average 22 to 30 cm.

*Depth*.—Average 8.0 cm.

Flower fragrance: None.

Corolla:

*Tepal arrangement*.—Single whorl, overlapping.

*Quantity*.—6 per flower.

*Shape*.—Lanceolate.

*Margin*.—Very slightly crenate, moderate undulation.

*Apex*.—Short apiculate.

*Base*.—Truncate.

*Texture*.—Smooth, velvety upper and lower surfaces.

*Length*.—Average Range 10.0 to 13.8 cm.

*Width*.—Average 2.8 cm.

Color:

*Tepals*.—When opening: Upper surface: Near RHS Violet-Blue 97A with median line near Red-Purple N66D. Lower surface: Near RHS Violet-Blue 96D with faint streaks near Red-Purple N74C. Fully opened: Upper surface: Near RHS Violet-Blue 92B with median line streak near Red-Purple 71B, streak much stronger near base. Lower surface: Near RHS Violet-Blue 92B with faint streaks near Red-Purple N74C. Ageing: Upper surface: Near RHS Violet-Blue 92B with median line near Red-Purple 71D. Lower surface: Near RHS Violet-Blue 92D with very faint streaks near Red-Purple 71D.

Bud:

*Shape*.—Elongated sphere.

*Length*.—Approximately 15 cm.

*Diameter*.—Approximately 7.6 cm.

*Color*.—Near RHS Violet-Blue 94C.

Pedicels:

*Length*.—Average range 9 to 15 cm.

*Width*.—Approximately 0.4 cm.

*Angle*.—Average 45° to 80°.

*Strength*.—Flexible.

*Color*.—Near RHS Green 138A flushed Greyed-Purple N187B.

REPRODUCTIVE ORGANS

Stamens:

*Number*.—Average 90 per flower.

*Anther length*.—Approximately 0.4 cm.

*Anther color*.—Near RHS Purple N79C.

*Anther shape*.—Oblong.

*Filament length*.—Approximately 1.5.

*Filament color*.—Near RHS Red-Purple 69D.

*Pollen quantity*.—Moderate.

*Pollen color*.—Greyed-Purple N87D.

Pistil:

*Length*.—Approximately 2.5 cm.

*Style length*.—Approximately 1.1 cm.

*Stigma*.—Shape: Fine irregular hairs. Color: Near RHS Green-White 157B.

OTHER CHARACTERISTICS

Seeds: Seed production not observed.

Disease/pest resistance: Neither resistance nor susceptibility to normal diseases and pests of *Clematis* has been observed.

Temperature tolerance: Tolerates temperatures from approximately −20° C. to 45° C.

What is claimed is:

1. A new and distinct cultivar of *Clematis* hybrid plant named 'TRA35' as herein illustrated and described.

* * * * *